(12) United States Patent
Candelaria et al.

(10) Patent No.: US 6,497,646 B1
(45) Date of Patent: Dec. 24, 2002

(54) INTRAVASCULAR RADIOTHERAPY SOURCE RIBBON HAVING VARIABLE RADIOPACITY

(75) Inventors: Roberto Candelaria, Homestead, FL (US); Benjamin David McDaniel, Newport Beach, CA (US)

(73) Assignee: Cordis Corporation, Miami Lakes, FL (US)

( * ) Notice: Subject to any disclaimer, the term of this patent is extended or adjusted under 35 U.S.C. 154(b) by 24 days.

(21) Appl. No.: 09/808,477

(22) Filed: Mar. 14, 2001

(51) Int. Cl.$^7$ .................................. A61N 5/00
(52) U.S. Cl. .................................. 600/7; 600/8
(58) Field of Search .......................... 600/7, 8

(56) References Cited

U.S. PATENT DOCUMENTS

| | | |
|---|---|---|
| 4,323,055 A | 4/1982 | Kubiatowicz |
| 4,454,795 A | 6/1984 | Ellis |
| 4,737,153 A | 4/1988 | Shimamura et al. |
| 4,994,013 A | 2/1991 | Suthanthiran et al. |
| 5,059,166 A | 10/1991 | Fischell et al. |
| 5,163,896 A | 11/1992 | Suthanthiran et al. |
| 5,199,939 A | 4/1993 | Dake et al. |
| 5,863,284 A | 1/1999 | Klein |
| 5,871,436 A | 2/1999 | Eury |
| 5,873,811 A | 2/1999 | Wang et al. |
| 5,882,291 A | 3/1999 | Bradshaw et al. |
| 5,899,882 A | 5/1999 | Waksman et al. |
| 5,976,067 A | 11/1999 | Tucker et al. |
| 6,007,475 A | 12/1999 | Slater et al. |
| 6,019,718 A | 2/2000 | Hektner |
| 6,036,682 A | 3/2000 | Lange et al. |
| 6,059,714 A | 5/2000 | Armini et al. |
| 6,077,213 A | 6/2000 | Ciezki et al. |
| 6,096,070 A | 8/2000 | Ragheb et al. |
| 6,103,295 A | 8/2000 | Chan et al. |
| 6,132,359 A | 10/2000 | Bolenbaugh |
| 6,149,574 A | 11/2000 | Tauthen et al. |
| 6,156,046 A | 12/2000 | Passafaro et al. |
| 6,159,143 A | 12/2000 | Lennox |

*Primary Examiner*—Gerald A. Michalsky
(74) *Attorney, Agent, or Firm*—Carl J. Evens

(57) ABSTRACT

A unidummy intravascular radiotherapy source ribbon assembly is utilized to properly align radioactive seeds in a radioactive intravascular radiotherapy source ribbon assembly to control the dose rate profile such that only the proper tissue is irradiated. The source ribbon assembly includes a core comprising one or more sections having a first radiopacity and one or more sections having a second radiopacity.

14 Claims, 1 Drawing Sheet

INTRAVASCULAR RADIOTHERAPY SOURCE RIBBON HAVING VARIABLE RADIOPACITY

BACKGROUND OF THE INVENTION

1. Field of the Invention

The present invention relates to intravascular radiotherapy source ribbon assemblies, and more particularly to unidummy intravascular radiotherapy source ribbon assemblies comprising non-radioactive materials of varying radiopacity for ascertaining the proper position for the placement of radioactive materials within the vasculature.

2. Discussion of the Related Art

Percutaneous transluminal coronary angioplasty (PTCA) is a therapeutic medical procedure used to increase blood flow through an artery and is the predominant treatment for coronary vessel stenosis. The increasing popularity of the PTCA procedure is attributable to its relatively high success rate and its minimal invasiveness compared with coronary by-pass surgery. Patients treated utilizing PTCA; however, may suffer from restenosis. Restenosis refers to the re-narrowing of an artery after a successful angioplasty procedure. Restenosis usually occurs within the initial six months after an angioplasty. Early attempts to alleviate the effect of restenosis included repeat PTCA procedures or by-pass surgery, with attendant high cost and added patient risk.

More recent attempts to prevent restenosis by use of drugs, mechanical devices, and other experimental procedures have limited long term success. Stents, for example, dramatically reduce acute reclosure and slow the effects of smooth muscle cell proliferation by enlarging the maximal luminal diameter, but otherwise do nothing substantial to slow the proliferative response to the angioplasty induced injury.

Restenosis is now believed to occur at least in part as a result of injury to the arterial wall during the lumen opening angioplasty procedure. In some patients, the injury initiates a repair response that is characterized by hyperplastic growth of the vascular smooth muscle cells in the region traumatized by the angioplasty. Intimal hyperplasia or smooth muscle cell proliferation narrows the lumen that was opened by the angioplasty, regardless of the presence of a stent, thereby necessitating a repeat PTCA or use of other procedures to alleviate the restenosis.

Recent studies indicate that intravascular radiotherapy (IRT) has promise in the prevention or long-term control of restenosis following angioplasty. Intravascular radiotherapy may also be used to prevent or delay stenosis following cardiovascular graft procedures or other trauma to the vessel wall. Proper control of the radiation dosage, however, appears to be important to inhibit or substantially arrest hyperplasia without causing excessive damage to healthy tissue. Underdosing will result in inadequate inhibition of smooth muscle cell hyperplasia, or possibly even exacerbation of hyperplasia and resulting restenosis.

Radiation therapy may also be utilized in the treatment of other diseases such as cancerous and non-cancerous tumors or other proliferative normal tissue disorders. In this type of therapy, the ultimate aim is to destroy the malignant tissue without causing excessive radiation damage to nearby healthy, and possibly vital tissue. This is difficult to accomplish because of the proximity of malignant tissue to healthy tissue.

Brachytherapy is a form of radiation treatment in which an ionizing radiation source, for example, an intravascular radiotherapy source ribbon assembly, is placed into or adjacent to a tumor or stenotic lesion. Although any number of radioactive substances and/or radioactive sources may be utilized in brachytherapy, Iodine-125 is currently a good candidate isotope for vascular brachytherapy. Iodine-125 has been used as a liquid or immobilized onto a variety of surfaces for diagnostic and therapeutic purposes. It has already been fashioned into a variety of shapes and used clinically for cancer treatment as briefly described above. One standard method for immobilizing Iodine-125 on to a solid surface is through electroplating. Currently, Iodone-125 is immobilized onto the surface of solid silver wires for a very secure bond and because silver is radiopaque and thus is easily seen under X-ray fluoroscopy. It is important that a radiopaque material such as silver is utilized as a substrate for the radioactive substance because proper positioning of the radioactive substance is critical to the success of any brachytherapy procedure. In order to ensure that the proper radiation dosage is delivered to the stenotic lesion or abnormal cell growth with minimal exposure of healthy tissue, precise placement of the radioactive substance is required. Accordingly, there is a need for a device that has substantially the same profile as an intravascular radiotherapy source ribbon assembly, but rather than containing radioactive materials, comprises the same substrate as well as markers of differing radiopacity to effectively map out the area or region under treatment.

SUMMARY OF THE INVENTION

The unidummy intravascular radiotherapy source ribbon assembly of the present invention provides a means for overcoming the difficulties associated with the devices currently in use as briefly described above.

In accordance with one aspect, the present invention is directed to a unidummy intravascular radiotherapy source ribbon assembly. The unidummy intravascular radiotherapy source ribbon assembly comprises a container defining a cavity and a core disposed within the cavity of the container. The core comprises one or more non-radioactive sections having a first radiopacity and one or more sections having a second radiopacity disposed between the one or more sections having a first radiopacity.

In accordance with another aspect, the present invention is directed to a unidummy intravascular radiotherapy source ribbon assembly. The unidummy intravascular radiotherapy source ribbon assembly comprises a container defining a cavity and a core disposed within the cavity of the container. The core comprises one or more non-radioactive sections having a first radiopacity and one or more non-radioactive sections having varying radiopacities different from the first radiopacity disposed between the one or more sections having a first radiopacity.

In accordance with another aspect, the present invention is directed to a method for positioning an intravascular radiotherapy source ribbon assembly at a treatment site. The method comprises introducing a unidummy intravascular radiotherapy source ribbon assembly having a core comprising one or more non-radioactive sections having a first radiopacity and one or more non-radioactive sections having a second radiopacity disposed between the one or more sections having a first radiopacity to the treatment site, subjecting the treatment site to X-ray fluoroscopy, and determining the proper position for the one or more non-radioactive sections having a first radiopacity relative to the treatment site.

The unidummy intravascular radiotherapy source ribbon assembly of the present invention comprises a combination of one or more markers interspersed between sections of material comprising the substrate onto which the radioactive material is disposed. The sections of material comprising the substrate have a certain radiopacity, and the one or more markers have a different radiopacity, preferably lower than the substrate material. The unidummy intravascular radiotherapy source ribbon assembly has substantially the same profile and characteristics as a "hot" or radioactive intravascular radiotherapy source ribbon assembly. In having substantially the same profile and characteristics, the unidummy assembly may be utilized to ensure that the path through the vasculature or other pathway in the body is free of obstructions or open to the site of radiation delivery without exposing the patient to unnecessary radiation. In addition, to achieve the best possible results, the radioactive source is preferably positioned to deliver radiation to the entire stenotic lesion or tumor and not to the surrounding or adjacent healthy tissue. Accordingly, the unidummy assembly may be utilized to properly size and position the radioactive seeds. Essentially, since the unidummy assembly utilizes sections of the material comprising the substrate onto which the radioactive material is disposed along with one or more markers having different radiopacities, the exact positioning for the "hot" intravascular radiotherapy source ribbon assembly may be determined without having to utilize the "hot" intravascular radiotherapy source ribbon assembly. Mapping the treatment site with the unidummy assembly thereby minimizes unnecessary radiation exposure.

The unidummy intravascular radiotherapy source ribbon assembly of the present invention provides for the safe and effective determination of the precise position coordinates for the "hot" intravascular radiotherapy source ribbon assembly as well as determining if the path thereto is free from obstruction. Since the unidummy assembly is configured and has the same profile as the "hot" assembly, it is easy for the doctor or other health care professional to utilize. In addition, since the "hot" intravascular radiotherapy source ribbon assembly is essentially identical to the unidummy assembly, the doctor or other health care professional may easily make the transition from one assembly to the other.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Figure 1:
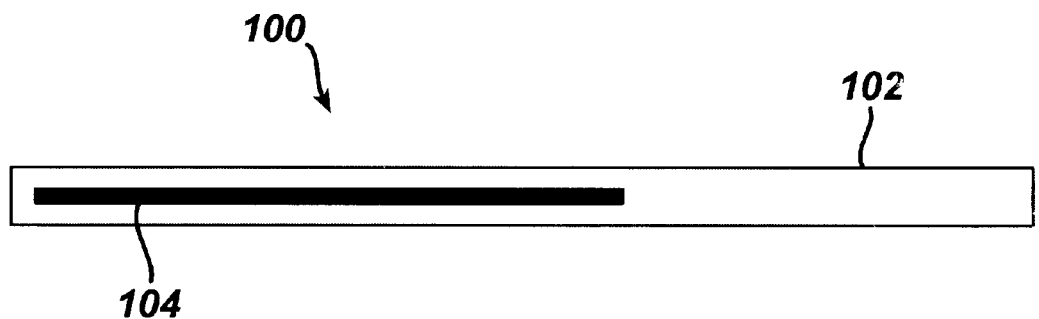
FIG. 1 is a cross-sectional representation of an exemplary unidummy intravascular radiotherapy source ribbon assembly in accordance with the present invention as it would appear to the naked eye.

The unidummy intravascular radiotherapy source ribbon assembly of the present invention comprises a source core, having one or more seed substrates and one or more markers disposed therebetween. The one or more seed substrates have a certain radiopacity and the one or more markers have a different radiopacity, preferably lower than that of the seed substrates. The source core or the unidummy intravascular radiotherapy source ribbon assembly, although it is made up of non-radioactive seeds and markers, and has substantially the same profile and characteristics as a "hot" or radioactive intravascular radiotherapy source ribbon assembly. Because the unidummy assembly has substantially the same profile and characteristics as the "hot" assembly, it may be safely utilized to determine the precise positioning coordinates for the "hot" assembly so that the radiation is directed at the stenotic lesion or tumor and not to the surrounding or adjacent healthy tissue. In having markers of varying radiopacity dispersed between the seed substrates, precise positioning and seed length may be determined under X-ray fluoroscopy. Once the precise position and sizing is determined, the "hot" source assembly may be constructed using the same pattern and sizes used in the unidummy assembly. All of this is accomplished without exposing the patient to unnecessary radiation.

A typical intravascular radiotherapy source ribbon assembly comprises a radioactive source disposed in a cavity of a substantially tubular container. The radioactive source may include any therapeutic amount of radioactive material appropriately distributed on a carrier body or core. The container is sealed at its ends and functions to isolate the radioactive substance from physical or chemical interchange between bodily fluids and the interior of the container, while at the same time permitting the radiation to pass through the walls of the container with minimum attenuation. The container, which may be formed from any number of suitable materials, including Nylon®, may be delivered to the site of the stenotic lesion or malignant cells by any number of suitable delivery devices, e.g. catheters, which are known in the art.

The carrier body or core may be formed from any suitable material which is detectable by X-rays for proper positioning in the body, and to which the requisite therapeutic amount of radioactive material may be attached. In the exemplary embodiments described below, the carrier body or core comprises at least one section or length of solid silver wire, or silver plated wire, and the radioactive material comprises radioisotopes such as Iodine-125 and Iodine-131. It is important to note that other radioactive substances may be utilized. Iodine-125, as stated above, is preferred because of its energetic emission of photons and its ability to strongly bond with silver.

Silver is the material of choice for a carrier body or core because it provides good X-ray visualization, which is important for proper positioning of the seed during therapy and because radioactive iodine may be easily attached to the surface thereof by chemical or electroplating processes. It is obvious that other X-ray opaque materials such as gold, copper and iron may be plated with silver to form a carrier body equivalent to a solid silver rod for purposes of the present invention. Similarly, silver metal may be deposited, chemically or by using sputtering and ion plating techniques, onto a substrate other than metal, for example, polymers such as polypropylene filament, provided that the thickness of the silver coating on the substrate exceeds about 0.050 mm to ensure adequate X-ray visualization.

Radioactive iodine may be attached to a silver substrate by a variety of suitable means, such as by first chloriding or bromiding the silver to form a layer of insoluble silver chloride or silver bromide, and then replacing the chloride or bromide ions with radioactive iodine ions by simple ion exchange. This process as well as other processes are well known in the relevant art.

In the typical intravascular radiotherapy source ribbon assembly, the radioactive source core may comprise a number of sections of radioactive material covered substrate wires. These individual sections are typically referred to as seeds. The seeds may be adjacent one another in the container or they may be spaced apart by any suitable means. The spacers serve two main functions. The first function is to space the "hot" seeds a sufficient distance to control the dose rate profile and lower the total radioactivity of the source core. The second function is to increase the flexibility of the intravascular radiotherapy source ribbon assembly.

The unidummy intravascular radiotherapy source ribbon assembly utilizes non-radioactive seeds formed from the same substrate as the radioactive seeds, described above, in combination with spacers having varying radiopacity. The non-radioactive seeds are identical to the radioactive seeds; namely, they are formed from the same materials, preferably, silver or silver coated materials, and have the identical profile. In this way, the unidummy intravascular radiotherapy source ribbon assembly may be utilized to map out the area of the body which is to undergo treatment without exposing the patient to unnecessary radiation. In addition, the unidummy assembly has the same profile and characteristics as the "hot" assembly; therefore, the doctor can use the unidummy assembly to determine if the path to the treatment site is free from obstructions.

FIG. 1 illustrates an exemplary embodiment of the unidummy, intravascular radiotherapy source ribbon assembly 100 in accordance with the present invention as it would appear to the naked eye. The unidummy intravascular radiotherapy source ribbon assembly 100 comprises a substantially tubular container 102, and a source core 104 disposed within the cavity defined by the container 102. The container 102 is sealed at both its proximal and distal ends to isolate the source core 104 and may be formed from any suitable biocompatible and radioactive emission transparent material. In addition, the container 102 is preferably flexible enough to navigate through narrow and/or tortuous pathways and stiff enough to traverse the same narrow and/or tortuous pathways. In the preferred embodiment, the container 102 is formed from Nylon®. The source core 104, as described above, comprises one or more seeds formed from silver wire or silver coated metallic or nonmetallic substrates. The cross-section of the silver wire may be varied to increase the surface area available on which to dispose the radioactive substance if these were to be "hot" seeds. Even though the source core is not radioactive, it preferably has the same profile as the radioactive source core for the reasons given above. In the unidummy assembly, non-radioactive seeds are utilized; however, while any number of radioactive materials may be utilized in the "hot" assembly without substantially changing the profile of the seeds, in the preferred embodiment Iodine-125 is utilized because of its energetic emission of photons and its ability to strongly bond with silver.

Figure 2:
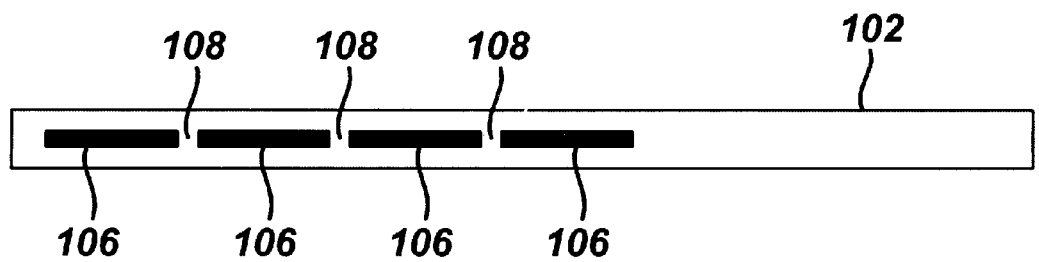
FIG. 2 is a cross-sectional representation of the exemplary unidummy intravascular radiotherapy source ribbon assembly illustrated in FIG. 1 as it would appear under X-ray fluoroscopy.

As stated above, FIG. 1 illustrates the assembly 100 as it would appear to the naked eye. This is true because the spacers have the same profile and shape as the seeds and thus would appear as a continuous core 104. FIG. 2, however, illustrates the exemplary embodiment of the unidummy intravascular radiotherapy source ribbon assembly 100 in accordance with the present invention as it would appear under X-ray fluoroscopy. As illustrated, the seeds 106 would appear darker than the spacers 108 due to their higher radiopacity. It is readily apparent that the radiopacity of the spacers 108 be greater than that of the seeds 106, but in the preferred embodiment, the seeds 106 have a greater radiopacity. This difference in radiopacity allows the physician or other health care provider to properly align the assembly 100 in the anatomy so that the intravascular radiotherapy source radioactive ribbon assembly may be positioned accurately and quickly.

Any number of materials may be utilized for the spacers 108 and would readily suggest themselves to those skilled in the relevant art. The spacers 108 may be modified to any size to ensure proper visualization under X-ray fluoroscopy. In addition, the spacers 108 may be formed from different materials having differing radiopacities such that they are arranged in an ascending or descending radiopacity order so that each treatment section has progressively lighter or darker radiopacity. Each of these modifications may be utilized to ensure the proper positioning of the radioactive seeds in the "hot" intravascular radiotherapy source ribbon assembly.

The seeds 106 and the spacers 108 may be of any size and may be positioned within the container 102 in any suitable configuration to ensure optimum radiation delivery. Accordingly, both the seeds 106 and spacers 108 are removably mounted within the container 102.

In use, a physician or other health care provider would deliver the unidummy intravascular radiotherapy source ribbon assembly 100 (FIGS. 1 and 2) to what he or she believes to be the proper treatment site. Under X-ray fluoroscopy, the physician would then determine the proper positioning for the "hot" seeds such that the radiation is directed to the desired tissues and not anywhere else. Once this mapping is completed, the unidummy assembly is removed and a "hot" assembly is configured to match the treatment areas determined by the unidummy assembly 100 and inserted into the treatment site. Since physicians mapped out the treatment area and ensured that the unidummy assembly 100 was able to reach the treatment area, it is a much more simple and safe procedure to insert the "hot" assembly and provide effective and safe treatment.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A unidummy intravascular radiotherapy source ribbon assembly comprising:
    a container defining a cavity; and
    a core disposed within the cavity of the container, the core comprising at least one section having a first radiopacity and at least one section having a second radiopacity disposed between the at least one section having a first radiopacity.

2. The unidummy intravascular radiotherapy source ribbon assembly according to claim 1, wherein the container comprises a radioactive emission transparent material.

3. The unidummy intravascular radiotherapy source ribbon assembly according to claim 1, wherein the at least one section having a first radiopacity each have a predetermined length and comprise a substrate for a radioactive substance.

4. The unidummy intravascular radiotherapy source ribbon assembly according to claim 3, wherein the at least one section having a second radiopacity each have a predetermined length, and the second radiopacity is less than the first radiopacity.

5. The unidummy intravascular radiotherapy source ribbon assembly according to claim 3, wherein the substrate comprises silver.

6. The unidummy intravascular radiotherapy source ribbon assembly according to claim 1, wherein the at least one section having a first radiopacity each have varying lengths and comprise a substrate for a radioactive substance.

7. The unidummy intravascular radiotherapy source ribbon assembly according to claim 6, wherein the at least one section having a second radiopacity each have varying lengths, and the second radiopacity is less than the first radiopacity.

8. The unidummy intravascular radiotherapy source ribbon assembly according to claim 1, wherein the at least one section having a first radiopacity and at least one section having a second radiopacity are removably mounted in the container.

9. The unidummy intravascular radiotherapy source ribbon assembly comprising:

a container defining a cavity; and a core disposed within the cavity of the container, the core comprising at least one non-radioactive section having a first radiopacity and at least one non-radioactive section having varying radiopacities different than the first radiopacity disposed between the at least one non-radioactive section having a first radiopacity.

10. The unidummy intravascular radiotherapy source ribbon assembly according to claim 9, wherein the at least one non-radioactive section having a first radiopacity each have a predetermined length and comprise a substrate for a radioactive substance.

11. The unidummy intravascular radiotherapy source ribbon assembly according to claim 9, wherein the at least one non-radioactive section having a first radiopacity each have varying lengths and comprise a substrate for a radioactive substance.

12. The unidummy intravascular radiotherapy source ribbon assembly according to claim 9, wherein the at least one non-radioactive section having varying radiopacities each have a predetermined length, and the varying radiopacities are less than the first radiopacity.

13. The unidummy intravascular radiotherapy source ribbon assembly according to claim 9, wherein the at least one non-radioactive section having varying radiopacities each have varying lengths, and the varying radiopacities are less than the first radiopacity.

14. A method for positioning an intravascular radiotherapy source ribbon assembly at a treatment site comprising:

introducing a unidummy intravascular radiotherapy source ribbon assembly having a core comprising at least one non-radioactive section having a first radiopacity and at least one non-radioactive section having a second radiopacity disposed between the at least one non-radioactive section having a first radiotherapy to the treatment site;

subjecting the treatment site to X-ray fluoroscopy; and determining the proper position for the at least one non-radioactive section having a first radiopacity relative to the treatment site.

* * * * *